(12) United States Patent
Pacetti et al.

(10) Patent No.: US 7,704,544 B2
(45) Date of Patent: Apr. 27, 2010

(54) SYSTEM AND METHOD FOR COATING A TUBULAR IMPLANTABLE MEDICAL DEVICE

(75) Inventors: Stephen D. Pacetti, San Jose, CA (US); Hung Manh Le, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1071 days.

(21) Appl. No.: 10/680,905

(22) Filed: Oct. 7, 2003

(65) Prior Publication Data

US 2005/0074544 A1 Apr. 7, 2005

(51) Int. Cl.
*B05D 1/00* (2006.01)

(52) U.S. Cl. .................. 427/2.24; 427/2.25; 427/428.01; 427/428.02

(58) Field of Classification Search ........... 424/426; 427/2.24; 118/218, 232, 233, 234, 244, 256, 118/257, 258, 261, 262, 264
See application file for complete search history.

(56) References Cited

U.S. PATENT DOCUMENTS

| | | |
|---|---|---|
| 4,007,680 A | 2/1977 | Pfleger et al. |
| 4,329,383 A | 5/1982 | Joh .................. 428/36 |
| 4,733,665 A | 3/1988 | Palmaz .............. 128/343 |
| 4,800,882 A | 1/1989 | Gianturco ........... 128/343 |
| 4,882,168 A | 11/1989 | Casey et al. ......... 424/468 |
| 4,886,062 A | 12/1989 | Wiktor ............... 128/343 |
| 4,941,870 A | 7/1990 | Okada et al. ........ 600/36 |
| 4,977,901 A | 12/1990 | Ofstead ............. 128/772 |
| 5,112,457 A | 5/1992 | Marchant ........... 204/165 |
| 5,165,919 A | 11/1992 | Sasaki et al. ........ 424/488 |
| 5,272,012 A | 12/1993 | Opolski ............. 428/423.1 |
| 5,292,516 A | 3/1994 | Viegas et al. ........ 424/423 |
| 5,298,260 A | 3/1994 | Viegas et al. ........ 424/486 |
| 5,300,295 A | 4/1994 | Viegas et al. ........ 424/427 |
| 5,306,501 A | 4/1994 | Viegas et al. ........ 424/423 |
| 5,328,471 A | 7/1994 | Slepian ............. 604/101 |
| 5,330,768 A | 7/1994 | Park et al. .......... 424/501 |
| 5,380,299 A | 1/1995 | Fearnot et al. ....... 604/265 |
| 5,417,981 A | 5/1995 | Endo et al. ......... 424/486 |
| 5,447,724 A | 9/1995 | Helmus et al. ....... 424/426 |
| 5,455,040 A | 10/1995 | Marchant ........... 424/426 |
| 5,462,990 A | 10/1995 | Hubbell et al. ....... 525/54.1 |

(Continued)

FOREIGN PATENT DOCUMENTS

EP 0 301 856 2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Erma Cameron
(74) *Attorney, Agent, or Firm*—Squire, Sanders & Dempsey, L.L.P.

(57) ABSTRACT

A system and method for coating a tubular implantable medical device, such as a stent, using an applicator and a coating composition are provided.

10 Claims, 8 Drawing Sheets

U.S. PATENT DOCUMENTS

| | | | |
|---|---|---|---|
| 5,464,650 A | 11/1995 | Berg et al. | 427/2.3 |
| 5,569,463 A | 10/1996 | Helmus et al. | 424/426 |
| 5,578,073 A | 11/1996 | Haimovich et al. | 623/1 |
| 5,605,696 A | 2/1997 | Eury et al. | 424/423 |
| 5,609,629 A | 3/1997 | Fearnot et al. | 623/1 |
| 5,624,411 A | 4/1997 | Tuch | 604/265 |
| 5,628,730 A | 5/1997 | Shapland et al. | 604/21 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,720 A | 7/1999 | Kataoka et al. | 525/523 |
| 5,955,509 A | 9/1999 | Webber et al. | 514/772.7 |
| 5,968,091 A * | 10/1999 | Pinchuk et al. | 623/1.16 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 23/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,203,551 B1 | 3/2001 | Wu | 6/108 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,610,087 B1 * | 8/2003 | Zarbatany et al. | 623/1.32 |
| 6,971,813 B2 * | 12/2005 | Shekalim et al. | 401/208 |
| 2001/0018469 A1 | 8/2001 | Chen et al. | 523/121 |
| 2001/0037145 A1 | 11/2001 | Guruwaiya et al. | 623/1.15 |
| 2002/0050220 A1 | 5/2002 | Schueller et al. | |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2003/0065377 A1 | 4/2003 | Davila et al. | 623/1.13 |
| 2003/0099712 A1 | 5/2003 | Jayaraman | 424/486 |
| 2004/0253366 A1 * | 12/2004 | Su et al. | 427/2.24 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 897 701 | 2/1999 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |

| | | |
|---|---|---|
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Coating Techniques, Air Knife Coating, http://www.ferron-magnetic.co.uk/coatings/airknife.htm, 1 page, printed Jul. 1, 2003.

Coating Techniques, Gravure Coating, http://www.ferron-magnetic.co.uk/coatings/gravure.htm, 2 pages, printed Jul. 1, 2003.

Coating Techniques, Reverse Roll Coating, http://www.ferron-magnetic.co.uk/coatings/revroll.htm, 2 pages, printed Jul. 1, 2003.

Coating Techniques, Gap Coating, http://www.ferron-magnetic.co.uk/coatings/knife.htm, 1 page, printed Jul. 1, 2003.

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2)131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

International Search Report and Written Opinion for a PCT application PCT/US2004/031185, filed Sep. 22, 2004, mailed Mar. 1, 2005, 14 pgs.

\* cited by examiner

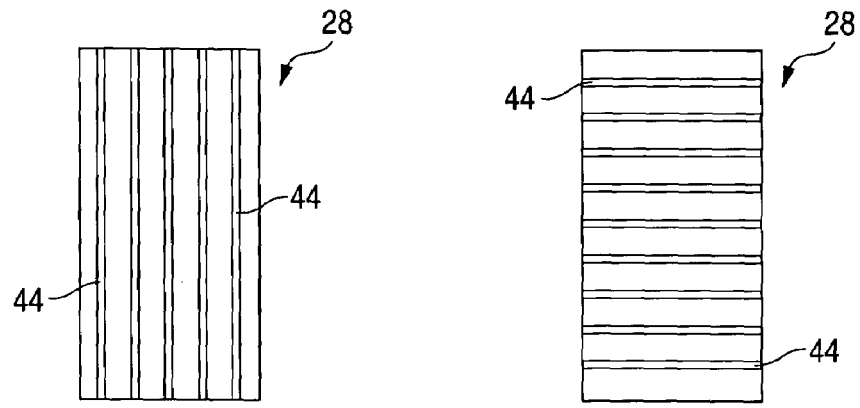
FIG. 6A    FIG. 6B
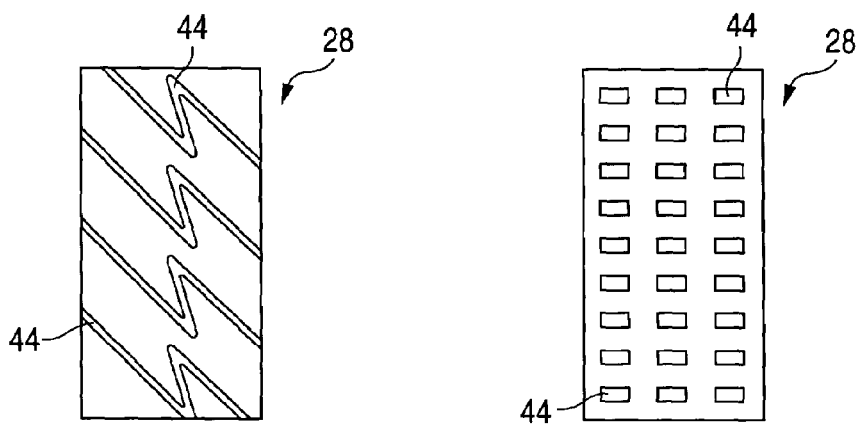
FIG. 6C    FIG. 6D
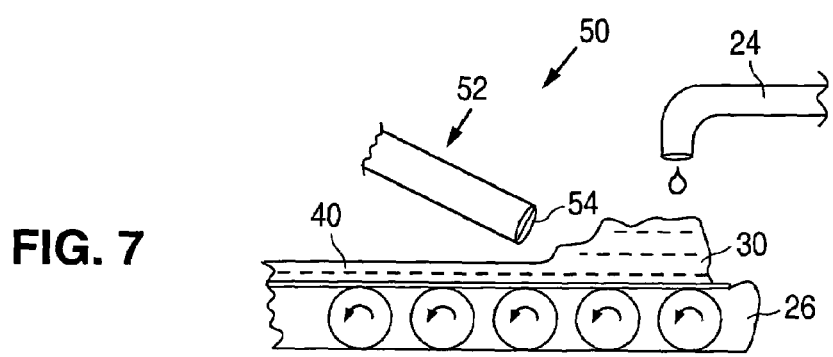
FIG. 7

US 7,704,544 B2

SYSTEM AND METHOD FOR COATING A TUBULAR IMPLANTABLE MEDICAL DEVICE

BACKGROUND OF THE INVENTION

1. Field of the Invention

This invention relates to a system for coating a tubular implantable medical device, such as a stent, and a method of coating a device using the system.

2. Description of the Background

Blood vessel occlusions are commonly treated by mechanically enhancing blood flow in the affected vessels, such as by employing a tubular implantable medical device known as a stent. Stents act as scaffoldings, functioning to physically hold open and, if desired, to expand the wall of the passageway. Stents are capable of being compressed, so that they can be inserted through small lumens via catheters, and then expanded to a larger diameter once they are at the desired location.

FIG. 1 illustrates a conventional stent 10 formed from a plurality of structural elements including struts 12 and connecting elements 14. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that can produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer.

As noted above, one of the methods of applying a drug composition to a stent involves spraying the composition onto the stent. The composition can be atomized to produce small droplets. Atomization is used because the droplet size can be made smaller than the size of the stent's structural elements, thus enabling a substantially conformal coating. However, there are potential shortcomings associated with a spray coating process. For instance, many of the drugs and polymers that are applied to stents are toxic when inhaled by humans. As the polymeric drug solutions are atomized, therefore, great care must be taken to avoid occupational exposure to the personnel conducting the process. Hoods, glove boxes, enclosures, and shrouds can be used to prevent toxic aerosol inhalation, but at a cost of decreased efficiency and increased expenditures on equipment. In light of these safety and manufacturing concerns, a stent coating method that avoids atomization of the coating can be advantageous.

Another disadvantage of a spray coating process is that the transfer efficiency can be comparatively low. Only droplets which fall onto the stent's structural elements are incorporated into the coating. If the spray pattern is larger than the stent, much of the spray can be wasted. Moreover, the stent's body can have a number of open spaces or gaps between the structural elements that allow the spray to pass through, and therefore be unused. The components of the coating compositions can be very expensive. For instance, many of the drugs applied to stents are small molecule agents or biologically derived substances such as peptides and gene therapy agents that are very costly. A stent coating method which transfers the coating solution in a more direct manner to the stent structure would therefore have a manufacturing cost advantage.

Yet another shortcoming of a spray coating process is that it can be difficult to direct the coating composition to a selected stent surface such as only onto the outer surface of the stent. The outer or tissue-contacting surface of the stent is the surface that is pressed against the vessel wall. Drug released from the outer surface of the stent is mostly diffused into the tissue, thereby maximizing the local delivery of the drug. Drug present on the inner or lumen contacting surface of the stent, on the other hand, can diffuse into the blood stream where it is transported by the blood flow to an area away from the site of stent implantation. For particular drugs, it may be advantageous to have a stent where the coating is only present on the outer surface of the stent. For example, certain drugs can produce adverse or even toxic side effects for the patient when they are released into the blood stream and carried into the vascular system. By having a drug coating limited to the outer surface of the stent, one can minimize the amount of these types of drugs that are delivered outside of the treatment area.

There are other reasons to produce a stent that only has the drug coating on the outer surface of the stent. In manufacturing drug eluting stents, one of the goals of the manufacturing process is to minimize the contribution of the coating to the stent dimensions (i.e., to minimize the thickness of the coating). By minimizing the thickness, or profile, of the stent's structural members, one can achieve better maneuverability as the stent is delivered to the site of implantation. Furthermore, because foreign materials in the body can elicit a chronic foreign body response, it is desirable to minimize the amount of polymer applied to the stent body. By applying the polymeric drug coating to only the outer surface of the stent, the amount of polymer exposed to the body of the patient can be reduced.

Spray or dip coating processes coat both the inner and outer surfaces of the stent. Masking techniques can be used to limit the coating application to the inner or outer surface. For example, a mandrel can be inserted through the longitudinal bore of the stent to mask the inner surface such that the coating is deposited only on the outer surface. It may be, however, desirable to coat the inner surface of the stent with a first type of drug, such as an angiogenic drug, and the outer surface with a second type of a drug such as one used for the treatment of restenosis. If the inner surface of the stent is first masked for the deposition of a coating on the outer surface of the strut, masking the coated outer surface of the stent to form a coating on the inner surface of the stent may cause damage to the coating on the outer surface. Accordingly, a shortcoming of the conventional coating techniques is the inability of manufacturers to coat the inner and outer surfaces of the stent with different pharmaceutical agents.

Another shortcoming of the above-described method of medicating a stent is the potential for coating defects. While some coating defects can be minimized by adjusting the coating parameters, other defects occur due to the nature of the application process. For example, during a spray coating process, a stent is commonly supported by a mandrel. Because the spray applicator sprays the entire surface of a stent as the composition is applied, and because there is a high degree of surface contact between the stent and the mandrel, there can be stent regions in which the liquid composition can flow, wick, and collect. Upon the removal of the coated stent from the mandrel, the excess coating may stick to the mandrel, thereby removing some of the coating from the stent in the form of peels as shown in FIG. 2, or leaving bare areas as shown in FIG. 3. Alternatively, as illustrated in FIG. 4, the excess coating may stick to the stent, thereby leaving excess coating as clumps or pools on the struts or webbing between the struts. These types of defects can cause adverse biological responses after the coated stent is implanted into a biological lumen. For instance, the tissue surrounding the biological lumen adjacent to the ends of stent 10 can adversely react to the coating defects (known as the "edge effect.")

Accordingly, the present invention provides a system and method for coating a tubular implantable medical device that addresses these needs.

SUMMARY OF THE INVENTION

In accordance with one aspect of the invention, a method of coating a tubular implantable medical device is provided, including forming a layer of a coating composition on a surface of an applicator, and transferring at least some of the layer of coating composition onto a tubular implantable medical device. In one embodiment, the layer has a thickness of about 2.5 microns to about 1000 microns. In another embodiment, the layer of the coating composition is transferred to an outer surface of the device. In yet another embodiment, the device is a stent.

In accordance with another aspect of the invention, a method of coating a tubular implantable medical device is provided, including forming a layer of a composition on a surface of an applicator substrate, and rotating a tubular implantable medical device along a longitudinal central axis of the device while a surface of the device is in close proximity to or in contact with a surface of the applicator substrate. In one embodiment, forming the layer of composition on the applicator substrate includes depositing a mass of the composition on the applicator substrate followed by leveling the composition so that the layer has a substantially uniform thickness. In another embodiment, the surface of the applicator substrate is substantially flat. In yet another embodiment, the applicator substrate is cylindrical in shape.

In a further aspect of the invention, a method of coating a tubular implantable medical device is provided, including depositing a layer of a composition on a surface of an applicator, positioning a tubular implantable medical device in close proximity to or in contact with the surface of the applicator, and rotating the applicator to deposit the composition on the tubular device. In one embodiment, the composition is applied to the outer surface of the device or the inner surface of the device but not both at the same time. In another embodiment, the method further includes rotating the device along a central longitudinal axis of the device.

In yet another aspect, a system for coating a tubular implantable medical device with a coating composition is provided, including an applicator substrate having a surface configured to receive a composition and to transfer the composition to a tubular implantable medical device, and a mandrel to support a tubular implantable medical device in close proximity to or in contact with the applicator substrate. In one embodiment, the system further includes an apparatus to rotate the mandrel. In another embodiment, the device includes a hollow, longitudinal bore, and the applicator is further configured to fit into the hollow, longitudinal bore of the device.

In a further aspect of the present invention, a system for coating a tubular implantable medical device with a coating composition is provided, including a reservoir holding a coating composition, an application roller configured to receive the coating composition from the reservoir, and a support element to support a tubular implantable medical device in close proximity to or in contact with the application roller. In one embodiment, the system further includes a metering roller in communication with the application roller. In another embodiment, the surface of the application roller has grooves.

BRIEF DESCRIPTION OF THE FIGURES

FIGS. 6A-6D are top views of applicator substrates in accordance with various embodiments;

FIG. 7 illustrates a system for leveling a coating composition in accordance with one embodiment of the present invention;

DETAILED DESCRIPTION

Tubular Implantable Medical Device

Figure 1:
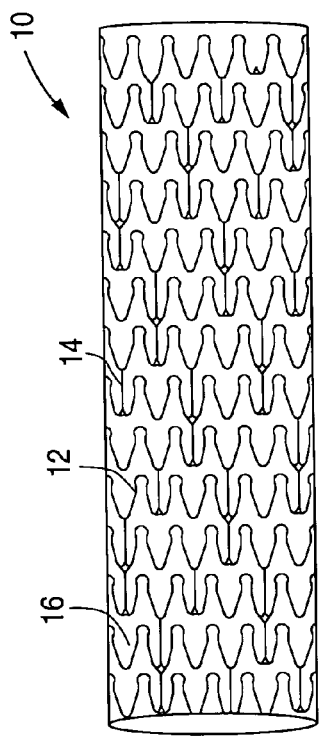
FIG. 1 illustrates a conventional stent.

Herein is disclosed a method and system for coating a tubular implantable medical device, such as a stent. In the interests of brevity, a method and system for coating a tubular stent including a polymeric coating are described herein. However, one of ordinary skill in the art will understand that other tubular medical devices having therapeutic capabilities can be coated using the system and method of the present invention. For example, the medical device can be a polymeric covering device such as a sheath.

Examples of tubular implantable medical devices for the present invention include self-expandable stents, balloon-expandable stents, stent-grafts, sheaths and grafts (e.g., aortic grafts). The underlying structure of the device can be of virtually any design. The device can be made of a metallic material or an alloy such as, but not limited to, cobalt chromium alloy, stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The device can also be made partially or completely from bioabsorbable or biostable polymers.

System and Method for Coating a Tubular Implantable Medical Device

As disclosed herein, a coating system can be used to coat a tubular stent by transferring a portion of a coating composition from the surface of an applicator onto a stent. The coating composition can be applied directly to the surface of the stent, or to a previously applied layer of a coating material. In one embodiment, referring to FIG. 5, a coating system 20 for coating a tubular stent 22 is illustrated to include a composition feeder 24 and an applicator 26 having an applicator substrate 28. Feeder 24 can be used to apply a coating composition 30 onto applicator substrate 28. Coating composition 30 can include a solvent and a polymer dissolved in the solvent. Coating composition 30 can also include an active agent.

Feeder 24 can be any suitable apparatus configured to deposit coating composition 30 onto applicator substrate 28. Representative examples of feeder 24 include a spray apparatus, a twin screw gravimetric feeder or a belt resin feeder. To realize greater process efficiency, coating composition 30 can be introduced into the process by means of individually metered, continuous mass flow streams through feeder 24. The flow rate of coating composition 30 from feeder 24 can be from about 0.02 mg/second to about 20 mg/second, for example about 1 mg/second.

As coating composition 30 is applied to stent 22, coating composition 30 should be in a substantially free-flowing or liquid form. The viscosity of coating composition 30 when applied onto stent 22 can be at the maximum of about 10 centipoises at ambient temperature and pressure to about 1000 centipoises at ambient temperature and pressure. The consistency of the coating composition can affect how the composition is received by stent 22.

Applicator substrate 28 can be capable of moving in a linear direction towards stent 22 as indicated by arrow 32 to deposit coating composition 30 on stent 22. Applicator 26, for instance, can be integrated with a plurality of conveyer rollers 34 that move applicator substrate 28 towards stent 22. In other words, to provide movement, applicator substrate 28 can be incorporated into a conveyer belt system that is a component of applicator 26. Applicator substrate 28 can be moved at about 1 mm/second to about 12 mm/second, for example about 6 mm/second.

Figure 5:
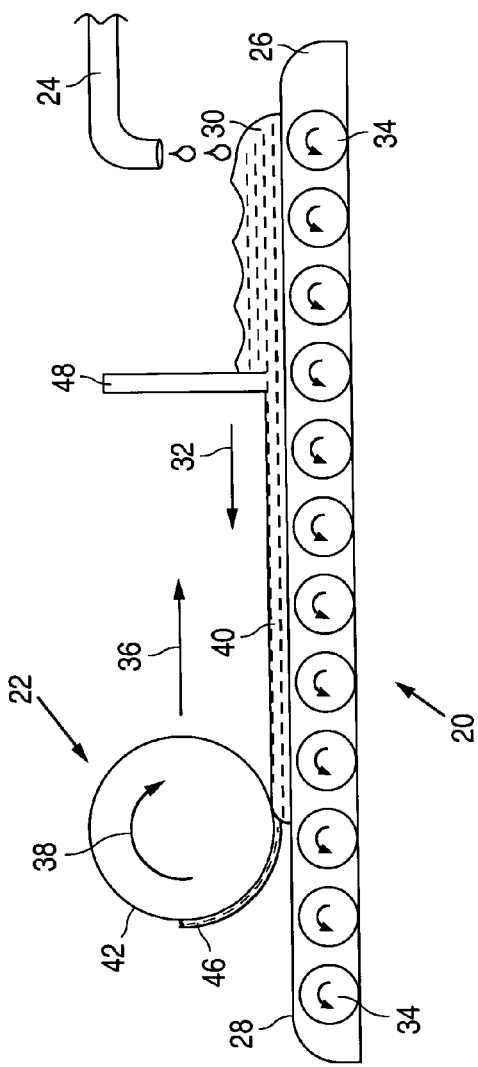
FIG. 5 illustrates a coating system for coating a stent in accordance with one embodiment of the present invention.
Figure 2:
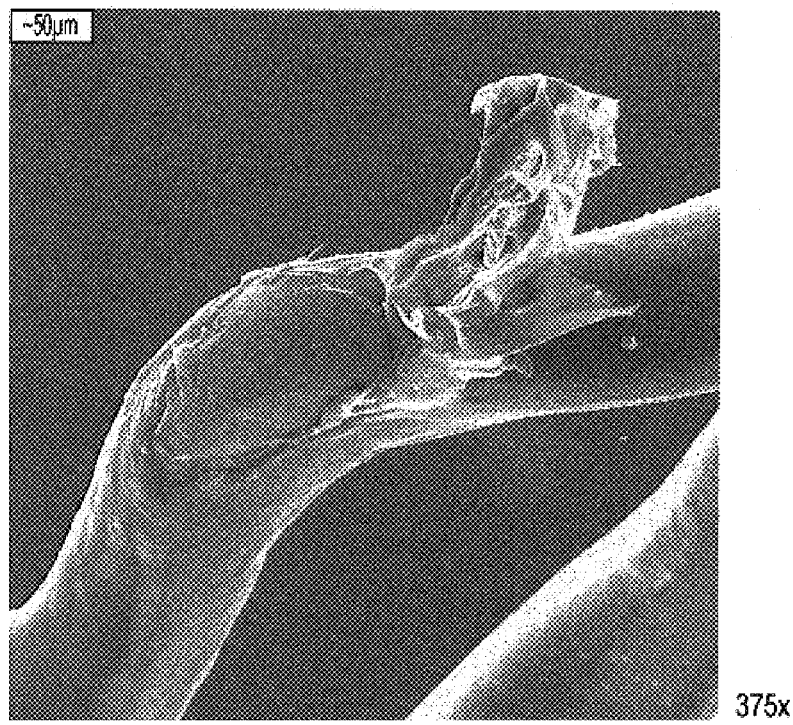
FIGS. 2-4 are scanning electron microscope images of stent coatings with coating defects.
Figure 3:
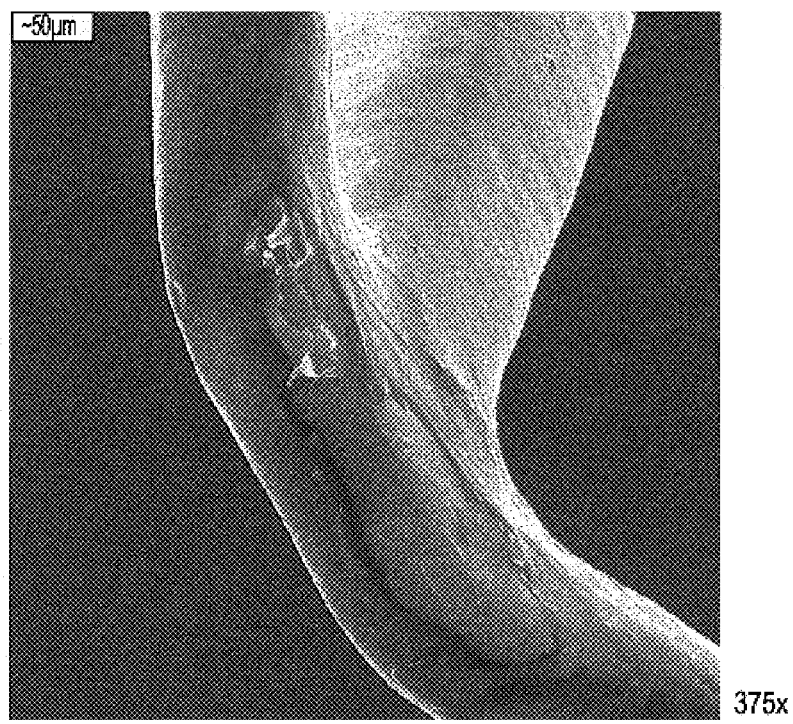

Stent 22 can be supported by a mandrel during the coating process. The mandrel can be used to position stent 22 in close proximity to or in contact with applicator substrate 28. The mandrel is configured to allow stent 22 to be rotated about a central longitudinal axis of stent 22 during the coating process. The mandrel can also be configured so that stent 22 can be rolled towards feeder 24 (i.e., moved in a linear direction as shown by arrow 36). As shown in FIG. 5, the rotational motion of stent 22 is depicted by arrow 38. Stent 22 can be rotated so that at least some of a layer 40 of coating composition 30 is transferred to outer surface 42 of stent 22. Rotational speed of stent 22 depends on the speed of applicator substrate 28, and can be, for example, from about 1 rpm to about 250 rpm, more narrowly from about 10 rpm to about 120 rpm. In one embodiment, the mandrel is connected to a motor that provides rotational motion to stent 22 during the coating process. In this embodiment, the rotation of stent 22 can drive applicator substrate 28.

Applicator substrate 28 has a surface capable of receiving a layer of the coating composition as deposited from feeder 24. In one embodiment, the surface of applicator substrate 28 includes grooves 44 to receive the coating composition. The surface of applicator substrate 28 can include grooves 44 having any suitable pattern. Referring to FIGS. 6A-6D, the surface of applicator substrate 28 can have vertical grooves 44 (FIG. 6A), horizontal grooves 44 (FIG. 6B), grooves 44 with a zigzag (FIG. 6C) and/or a discontinuous (FIG. 6D) pattern.

In one embodiment, applicator substrate 28 is substantially flat, and without any curvatures along the length of applicator substrate 28 wherein stent 22 is coated. By providing a substantially flat surface for applicator substrate 28, the thickness of coating 46 applied to stent 22 can be substantially uniform. Applicator substrate 28 can be made of a material that is flexible so that applicator substrate 28 can be a component of the conveyer belt system as illustrated in FIG. 5. In one embodiment, applicator substrate 28 can be made of a material that is "non-stick," having a low friction coefficient. The material should be resistant to solvents and heat, which may be directed onto applicator substrate 28 during the coating process. Representative examples of materials that can be used for applicator substrate 28 include polyurethanes, polyetheretherketone, polytetrafluoroethylene (Teflon™), Delrin™, Rulon™, Pebax™, Kynar™, Solef™, fluorinated ethylene-propylene copolymer, poly(vinylidene fluoride-co-chlorotrifluoroethylene), poly(vinyl fluoride), poly(ethylene terephthalate) (MYLAR), polyesters, or any suitable nylon.

Coating system 20 can include a leveling bar 48 to produce a substantially uniform thickness for layer 40. Leveling bar 48 can be supported by any suitable structure and positioned at a set distance from applicator substrate 28 to define an opening through which coating composition 30 is passed. The size of the opening is generally comparable with the thickness of layer 40 on the stent side of leveling bar 48. Representative examples of the thickness of layer include about 2.5 microns to about 1000 microns. In one embodiment, the thickness is about 25 microns to about 100 microns.

Referring to FIG. 7, a leveling system 50 that includes an air gun 52 can be used to level coating composition 30. Air gun 52 can be capable of producing and directing an air flow to composition 30 applied to applicator substrate 28. The air flow can be of sufficient force to reduce the profile of the composition mass that has been applied to applicator substrate 28, and therefore level the composition to provide a substantially uniform thickness. Air gun 52 can have a nozzle 54 with a relatively narrow slit to help provide the sufficient force. Use of air gun 52 can be especially appropriate if coating composition 30 does not contain a highly volatile solvent, and has a low viscosity. By way of example, the air flow velocity from air gun 52 can be from about 10 meters/second to about 400 meters/second, more narrowly about 20 meters/second to about 200 meters/second.

Figure 8:
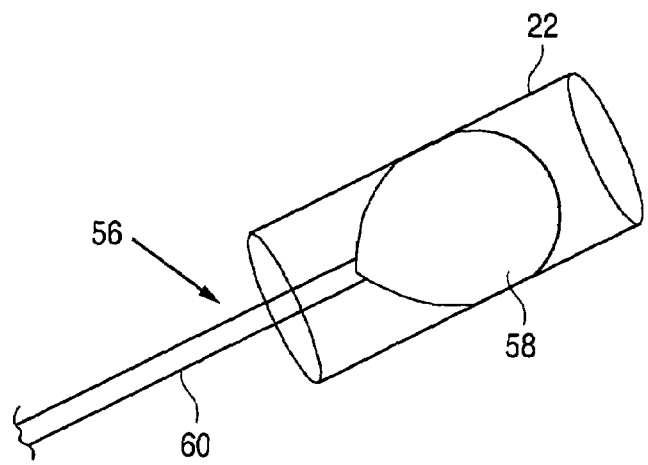
FIG. 8 is a perspective view of a support assembly for a stent to be used during a coating process.

The mandrel can have any design that is suitable to support stent 22 during the coating process. Referring to FIG. 8, stent 22 can be integrated with a mandrel 56 that includes a plug 58 positioned at a distal end of a stem 60. Plug 58 can be circular in cross-section making contact with the inner surface of the stent. Plug 58 can have an almost equivalent diameter to the inner diameter of stent 22 as positioned on mandrel 56 so as to allow a friction fit between plug 58 and stent 22. By way of example, the outer diameter of the plug 58 can be from about 1 mm to about 8 mm. Plug 58 can also have other cross-sectional shapes.

Plug 58 can be made of materials that are rigid or semi-pliable. The material can be a "non-stick" material having a low friction coefficient and should be resistant to solvents and heat, which may be directed onto plug 58 during the coating process. Representative examples of materials that can be used for plug 58 include the same materials listed above for applicator substrate 28 as well as rigid materials such as stainless steel, titanium alloys, cobalt-chromium alloys, ceramics, metallic carbides, inorganic carbides, and nitrides.

In addition to a single plug 58, stent 22 can also be held by other support designs. For example, stent 22 can be supported by two plugs, one at each end of stent 22. The two plugs in this type of support apparatus could be connected by an internal mandrel. Alternatively, the two plugs could be unconnected having their relative orientation maintained by an external fixture. The two end plugs can be conical in shape, and therefore, contact stent 22 at contact points at the end struts.

As coating composition 30 is applied using coating system 20, the temperature of coating composition 30 can be controlled during the coating process. In one embodiment, coating system 20 includes a temperature controller for heating or cooling coating composition 30. The temperature controller can be used to heat or cool coating composition 30 in order to produce and maintain a coating consistency that is suitable for coating composition 30. Additionally, the temperature controller can be used to cool coating composition 30 especially if a volatile solvent is one of the components of coating composition 30. The temperature controller can include any suitable apparatus for heating or cooling the coating composition, and can be in communication with any suitable component of coating system 20. In one embodiment, applicator substrate 28 is in communication with the temperature controller so that the temperature controller can modify the temperature of coating composition 30 during the coating process, for example as coating composition is deposited from feeder 24. In another embodiment, mandrel 56 is in communication with the temperature controller so that the temperature controller can modify the temperature of stent 22 during the coating process.

Figure 9:
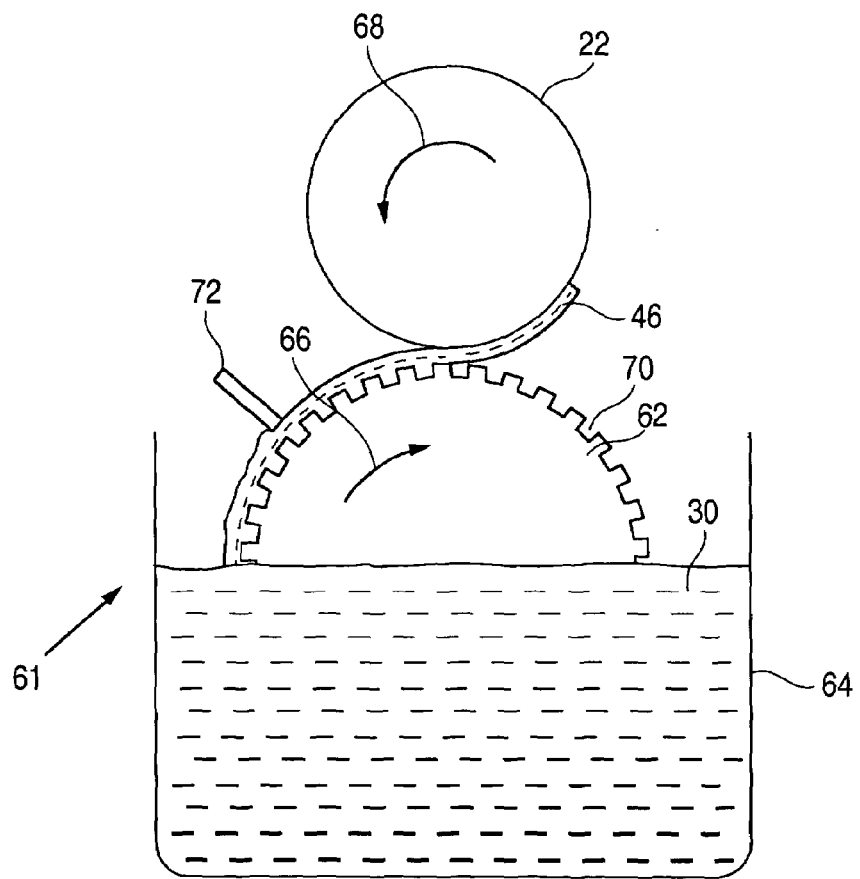
FIGS. 9-13 illustrate coating systems for coating a stent in accordance with various other embodiments of the present invention.

In another embodiment of the present invention, referring to FIG. 9, a coating system 61 including an application roller 62 can be used to apply a layer of composition to the outer surface of stent 22. Stent 22 can be supported by a mandrel so that stent 22 is in close proximity to or in contact with application roller 62. Referring to FIG. 9, application roller 62 is partially submerged in a coating composition disposed in a reservoir 64. The viscosity of the coating composition in reservoir 64 can be at the maximum, about 10 centipoises to about 10,000 centipoises at ambient temperature and pressure. As application roller 62 rotates, the coating composition is transferred from application roller 62 to stent 22.

Application roller 62 can be capable of rotating as indicated by arrow 66, while stent 22 can be rotated as indicated by arrow 68. As application roller 62 is rotated, a layer of coating composition is deposited onto the outer surface of application roller 62. In one embodiment, application roller 62 can include grooves or pores 70 that facilitate the transfer of the composition from reservoir 64 to the outer surface of application roller 62. In another embodiment, application roller 62 is completely smooth or only slightly textured. In yet another embodiment, application roller 62 is surfaced with bristles, fibers, brushes, or other absorbent materials, including sponge or sponge-like material.

In one embodiment, application roller 62 is cylindrical in shape. Application roller 62 can have an outer circumference with a radius of curvature about equal to the radius of curvature of the outer circumference of stent 22. Also, the outer diameter of application roller 62 can be larger than the outer diameter of stent 22. By way of example, the outer diameter of application roller 62 can be from about 3 mm to about 50 mm for a stent having an outer diameter of about 1 mm to about 8 mm. Since stent 22 is radially expandable, when referring to the diameter stent 22, the measurement is the diameter of stent 22 as positioned on a fixture during the coating process.

Rotation of application roller 62 and stent 22 are arranged so that the tangential velocities at the stent and roller surfaces are similar. The rotational speeds can therefore differ according the difference between the radius of application roller 62 and the radius of stent 22. Rotation of stent 22 can be from about 1 rpm to about 200 rpm, more narrowly from about 2 rpm to about 30 rpm. Since application roller 62 can have a larger diameter than stent 22, rotation of application roller 62 can be from about 0.02 rpm to about 500 rpm, more narrowly from about 0.04 rpm to about 80 rpm.

Coating system 61 can also include a leveling blade 72 to produce a substantially uniform thickness on the outer surface of application roller 62. Leveling blade 72 can be supported by any suitable structure and can be positioned at a set distance from application roller 62 to produce a selected thickness for the composition applied to the surface of application roller 62. Coating system 61 can include a temperature controller. Any suitable component of coating system 61 can be in communication with the temperature controller, such as the mandrel supporting stent 22, application roller 62 and/or reservoir 64. A motor can be used to drive application roller 62 or stent 22.

Figure 10:
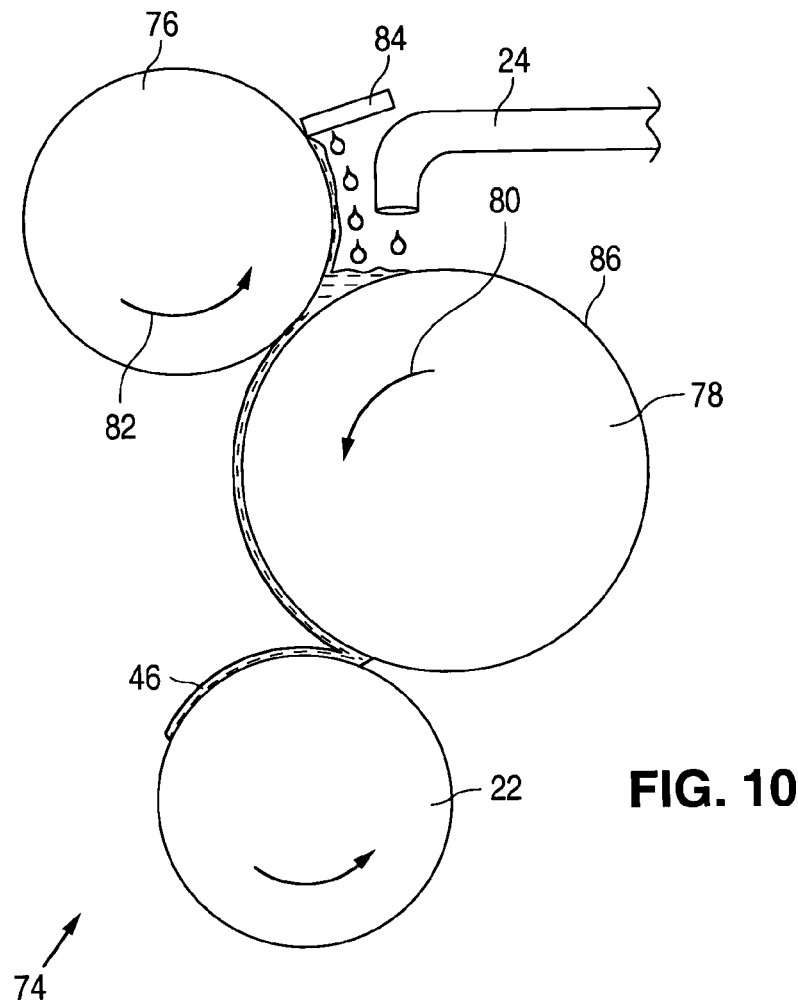

In another embodiment, referring to FIG. 10, a coating system 74 can have a metering roller 76 positioned in close proximity to an application roller 78. In one embodiment, application roller 78 and/or metering roller 76 are cylindrical in shape. Application roller 78 can have an outer surface configured to receive a composition from feeder 24. Application roller 78 can be capable of rotating as illustrated by arrow 80. Metering roller 76, in turn, can be capable of rotating as shown by arrow 82. The rotational direction of metering roller 76 can be opposite from the direction of application roller 78 to provide a controlled deposition of coating composition 30 onto the surface of application roller 78. Coating system 74 can further include a barrier 84 positioned in close proximity to the outer surface of metering roller 76. Barrier 84 can be supported by any suitable structure and can be used to prevent excess composition from being carried away by metering roller 76 as metering roller 76 is rotated.

Feeder 24 can be any suitable apparatus configured to deposit coating composition 30 onto application roller 78. As an alternative or in addition to feeder 24, application roller 78 can be configured to have an internal deposition system capable of depositing the coating composition onto the outer surface of application roller 78. For example, application roller 78 can include an open pore network in communication with a composition reservoir disposed in the interior of application roller 78. A pressure applied to the reservoir within application roller 78 can force the composition from the reservoir to outer surface 86.

Coating system 74 can include a temperature controller. Any suitable component of coating system 74 can be in communication with the temperature controller, such as the mandrel supporting stent 22, feeder 24, application roller 78, and/or metering roller 76. As noted above, the temperature controller can be used to heat or cool coating composition 30 as appropriate.

Figure 11:
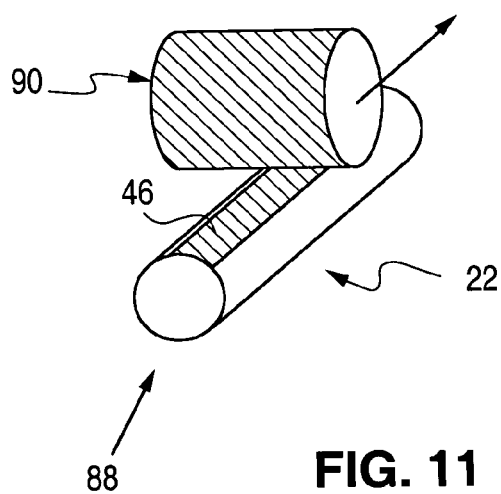

In another embodiment of the present invention, referring to FIG. 11, a coating system 88 can have an application roller 90 that is used to apply a coating composition along the length of stent 22. The coating composition can be applied to the surface of application roller 90 by the methods as described herein. The composition can also be applied by dipping application roller 90 into a coating composition prior to the coating of stent 22. Application roller 90 can then be rolled along the length of stent 22 to apply a stripe of coating composition. Stent 22 can be mounted on a mandrel that is capable of maintaining a fixed position for stent 22 as application roller 90 is applying the composition. Once application roller 90 has completed one pass along the length of stent 22, stent 22 can be rotated, and then application roller 90 can apply another stripe of coating composition to stent 22. Coating system 88 can include a temperature controller. Any suitable component of coating system 88 can be in communication with the temperature controller, such as the mandrel supporting stent 22, or application roller 90.

Figure 12:
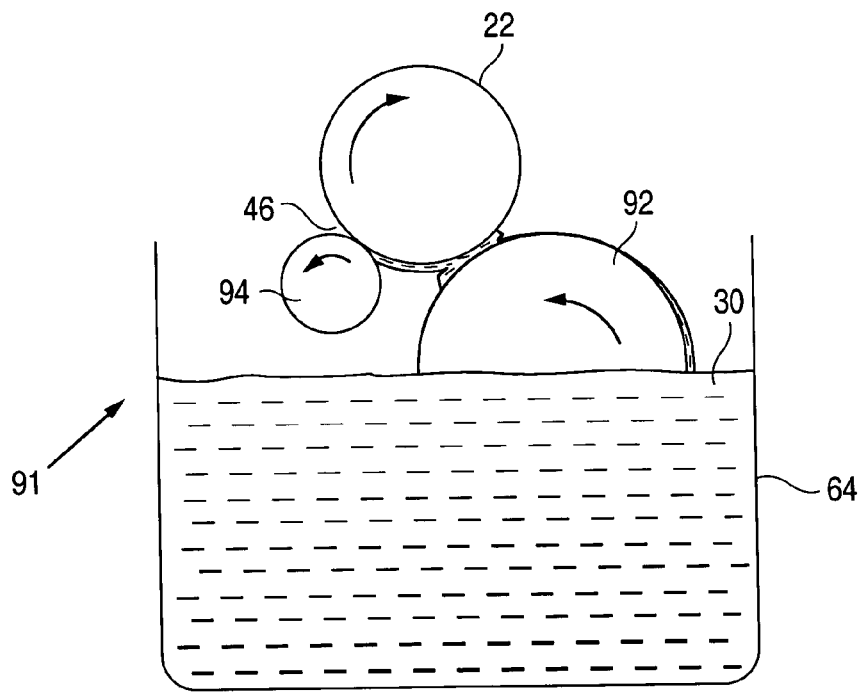

In a further embodiment, referring to FIG. 12, a coating system 91 including an application roller 92 and a support roller 94 can be used to apply a layer of composition to the outer surface of stent 22. Application roller 92 is partially submerged in reservoir 64. As application roller 92 and stent 22 are rotated, application roller 92 receives coating composition 30 from reservoir 64, and transfers coating composition 30 to stent 22. Coating system 91 can also have an optional leveling bar positioned in close proximity to the surface of application roller 92. For example, the leveling bar can be located at a position where the coated surface of application roller 92 emerges from reservoir 64. In this embodiment, instead of being supported by a mandrel, stent 22 can be supported by application roller 92 and support roller 94 during the coating process. Additionally, support roller 94 can be rotated to provide rotational motion to stent 22 during the coating process. Coating system 91 can also include a temperature controller.

Figure 13:
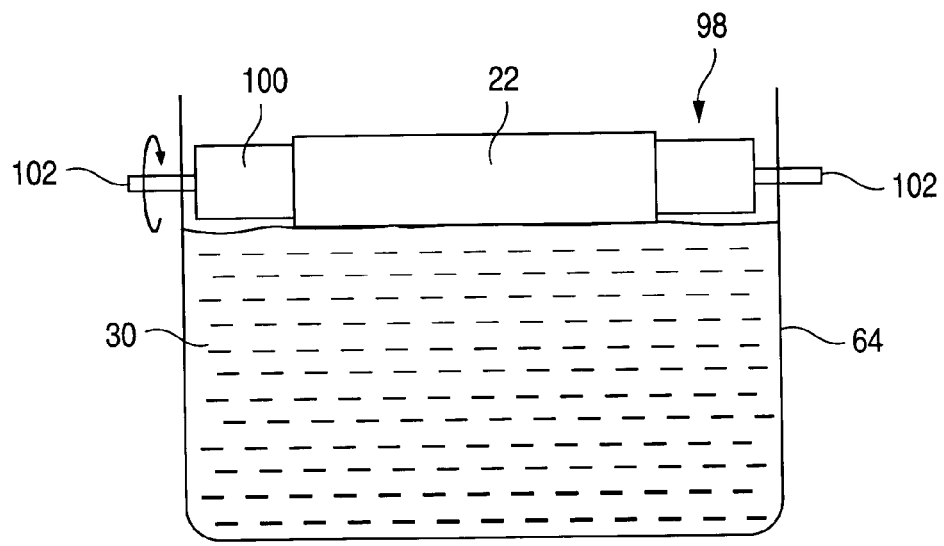

Referring to FIG. 13, in another embodiment, a coating system 96 can be used to coat stent 22. Coating system 96 includes reservoir 64 and a support assembly 98 that is connected to a rotating apparatus. Support assembly 98 includes a mandrel 100 and stems 102. For the coating process using coating system 96, stent 22 is partially submerged into coating composition 30 along the longitudinal length of stent 22. Stent 22 is then rotated while in a substantially horizontal position to coat stent 30 with coating composition 30.

As illustrated by FIG. 13, by using support assembly 98, stent 22 can be positioned so that only the outer surface of stent 22 is in contact with the surface of coating composition 30 as disposed in reservoir 64. The coating process can include rotating stent 22 while the outer surface of stent 22 barely touches coating composition 30. By precisely positioning stent 22, the outer surface of stent 22 can be coated without coating the inner surface of stent 22.

The method of using coating system 96 can include selecting process parameters that account for the viscosity and surface tension of coating composition 30. Coating composition 30 that is applied using coating system 96 has a viscosity range that is lower than the viscosity range of coating composition 30 as applied using the other embodiments described herein. The viscosity is lower so that coating composition 30 can coat in a conformal manner onto stent 22 as stent 22 is rotated. The viscosity for coating composition 30 for this embodiment can be about 2 centipoises at ambient temperature and pressure to about 500 centipoises at ambient temperature and pressure. The viscosity of coating composition 30 in reservoir 64 can be adjusted by selecting solutes (e.g., polymers) having a lower molecular weight, increasing the ratio of solvent to solute of coating composition 30, selecting a solvent that more effectively dissolves the solute, and/or adjusting the temperature via a temperature controller in communication with reservoir 64. For instance, the temperature controller can heat coating composition 30 in reservoir 64 in order to decrease the viscosity of coating composition 30. Additionally, the surface tension can be lowered by using additives in coating composition 30 such as surfactants, selecting an appropriate solvent and/or adjusting the temperature of reservoir 64. For instance, raising the temperature of coating composition 30 to near the solvent boiling point will lower the surface tension, allowing the coating to be more conformal and reduce the webbing produced by the process.

Figure 14A:
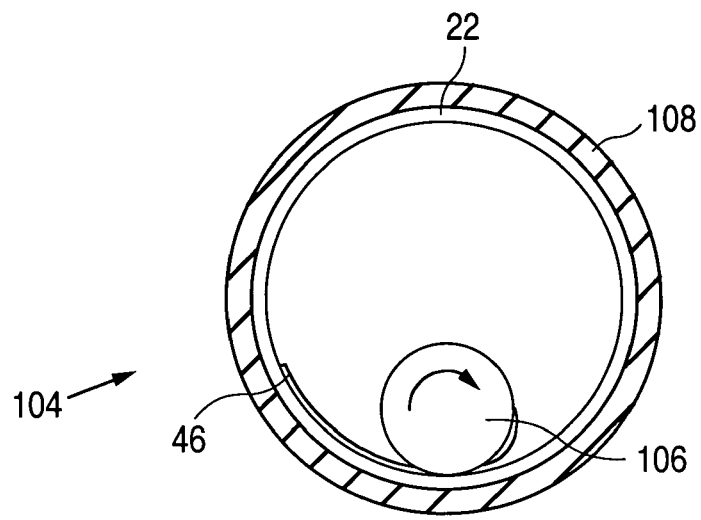
FIGS. 14A and 14B illustrate a coating system for coating an inner surface of a stent in accordance with an embodiment of the present invention.
Figure 14B:
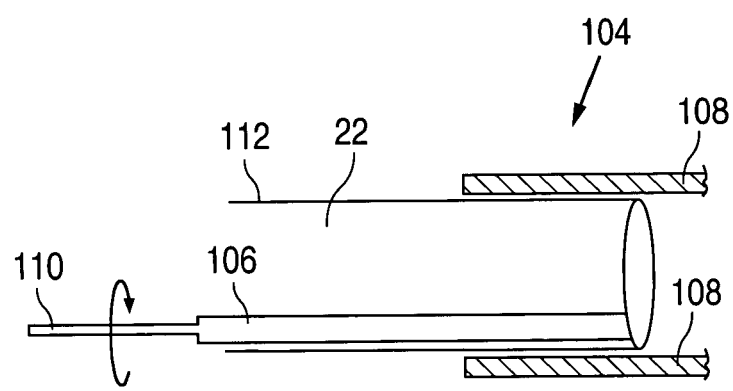

In another embodiment, a system is provided for coating an inner surface of stent 22. Coating just the inner surface can be advantageous for the delivery of therapeutic agents to the blood system to prevent thrombosis or promote rapid reendothelialization. For instance, certain drugs may effectively treat cardiovascular injuries when carried away by the blood flow to an area adjacent to the site of stent implantation. These drugs, for example, may be used to treat "edge restenosis." Referring to FIGS. 14A and 14B, a coating system 104 includes a stent 22 and an application roller 106. The outer surface of application roller 106 can be coated with a wet coating by dipping, or other coating methods as described herein, before contacting the inner surface of stent 22. Application roller 106 can then be inserted into the longitudinal bore of stent 22 and rolled around the inner circumference of stent 22. As with the above described embodiments, coating system 104 can include a temperature controller for heating or cooling coating composition 30 during the coating process.

Application roller 106 can have a smooth surface, or be coated with an absorbent material to facilitate loading the outer surface of applicator roller 106 with the coating composition. Application roller 106 can be supported by a stem 110. Stent 22, in turn, can be supported in a tube 108. Tube 108 can have an inner diameter that is slightly larger than the outer diameter of stent 22 and masks an outer surface 112 of stent 22. Application roller 106 can be sized to provide an effective circumference to deliver a coating composition to the inner surface of stent 22. By way of example, the outer diameter of application roller 106 can be from about 0.5 mm to about 5 mm for a stent having an inner diameter of about 0.9 mm to about 9.9 mm. In one embodiment, application roller 106 and/or tube 108 are in communication with a temperature controller.

Multiple repetitions for applying the coating composition can be performed using the system and method of the present invention. The amount of composition applied by each repetition can be about 1 microgram/cm$^2$ (of stent surface) to about 100 micrograms/cm$^2$, for example less than about 10 micrograms/cm$^2$ per application. Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2-4 hours) or by the application of warm air. The application of warm air between each repetition prevents coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds.

Any suitable number of repetitions of applying the composition followed by removing the solvent(s) can be performed to form a coating of a desired thickness or weight. The coating process as described herein can be used to form a coating on the stent having a thickness of about 0.5 microns to about 100 microns, more narrowly, about 1 micron to about 20 microns.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

The stent can be at least partially preexpanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

Coating Composition

As noted above, the coating composition can include a solvent and a polymer dissolved in the solvent, and optionally an active agent. Representative examples of polymers that can be used to coat a medical device in accordance with the present invention include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride, polyvinylidene chloride poly(vinylidene fluoride-co-hexafluoropropene), and poly(vinylidene fluoride-co-chlorotrifluoroethylene); polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site.

By using the system and method of the present invention, the same active agent can be applied to the inner and outer surfaces of stent 22. Alternatively, different active agents can be applied to the two surfaces. For example, the outer surface of stent 22 can be coated with a drug that is capable of treating restenosis. The inner surface of stent 22, on the other hand, can be coated with an angiogenic drug.

Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is pemirolast potassium. Other therapeutic substances or agents which may be appropriate include alpha-interferon, genetically engineered epithelial cells, dexamethasone and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

Example

Some embodiments of the present invention are illustrated by the following Example. The Example is being given by way of illustration only and not by way of limitation. The parameters and data are not be construed to unduly limit the scope of the embodiments of the invention.

A 20% EVAL solution in N,N-dimethlyacetamide (DMAC) (w/w) was prepared. A bead of the solution was applied to the surface of a stainless steel (316L) coupon. The bead was formed into a thin film by dragging a glass slide, held lengthwise, down the length of the coupon. A 12 mm VISION stent (Guidant Corporation) was expanded to 0.069 inches (1.75 mm) (inner diameter), mounted onto a section of a thin walled stainless steel tubing with an outer diameter of 0.07 inches (1.78 mm). The stent was then carefully laid down at one end of the thin film of polymer solution. The stent was rolled along the wet polymer film to coat the entire circumference of the outer surface of the stent. The stent was baked at 80° C. for one hour. After baking, the stent was removed from the tube.

Figures 4, 15:
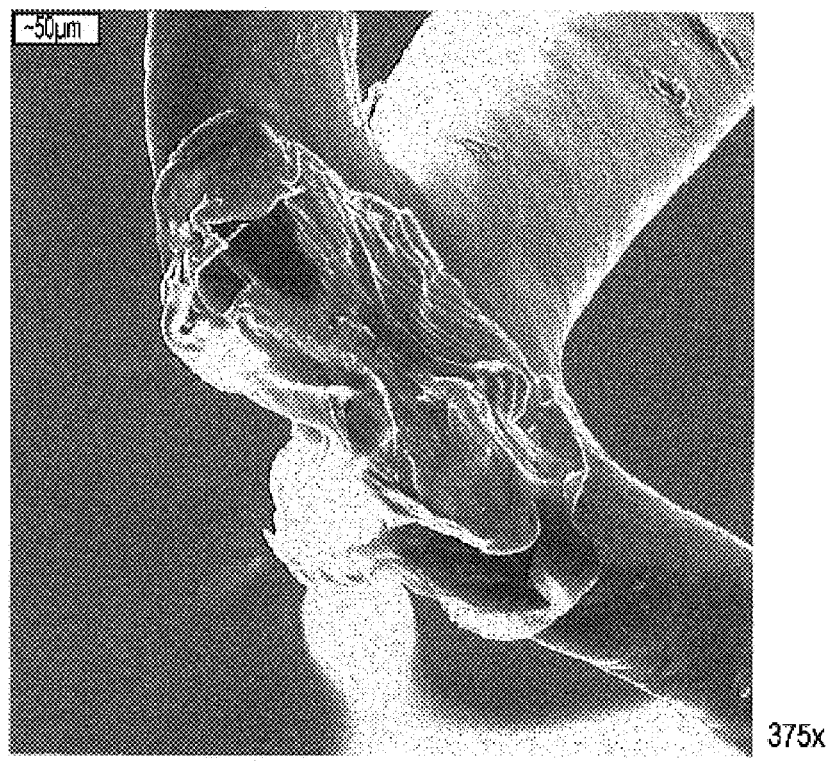
FIG. 15 is a scanning electron microscope image of a stent coating in accordance with the Example.

The stent was weighed and it was determined that the process applied a polymeric coating of 70 μg. The coating was then studied using a Scanning Electron Microscope (SEM) to view the distribution of the coating and to determine if there were visible coating defects as a result of the coating process. As illustrated in FIG. 15, the coating was limited to the outer surface of the stent and there were substantially no visible coating defects.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a tubular implantable medical device having a length and a longitudinal axis, comprising depositing a coating composition on an applicator, rotating the applicator in a first direction over the length of the device to apply a first stripe of coating composition to a surface of the device, rotating the device in a second direction about its longitudinal axis, and then applying a second stripe of coating composition to the surface of the device, wherein the rotating in the second direction is about an axis that is not parallel to a rotation axis of the applicator.

2. The method of claim 1, wherein a layer of coating composition on the surface of the applicator has a thickness of about 2.5 microns to about 1000 microns.

3. The method of claim 1, wherein a layer of coating composition on the surface of the applicator has a thickness of about 25 microns to about 100 microns.

4. The method of claim 1, wherein a layer of coating composition is transferred to an outer surface of the device.

5. The method of claim 1, wherein the viscosity of the coating composition is about 10 centipoises at ambient temperature and pressure to about 1000 centipoises at ambient temperature and pressure.

6. The method of claim 1, wherein the device is a stent.

7. The method of claim 1, wherein the coating composition further comprises a therapeutic substance.

8. The method of claim 1, wherein the depositing a coating composition on the applicator step includes leveling the composition so that a layer of coating composition has a uniform thickness.

9. The method of claim 1, wherein the device is supported on a mandrel.

10. The method of claim 1, wherein the applicator is partially submerged in a reservoir comprising a polymer and a solvent.

* * * * *